(12) United States Patent
Brubaker et al.

(10) Patent No.: US 8,349,806 B2
(45) Date of Patent: Jan. 8, 2013

(54) METHOD OF TREATING BLEPHARITIS

(75) Inventors: Kurt E. Brubaker, Eagle Point, OR (US); Romulus K. Brazzell, Morrisville, NC (US); Reza M. Haque, Randolph, NJ (US); John C. Ice, Jr., Wake Forest, NC (US); José L. Boyer, Chapel Hill, NC (US); Joseph B. Boyd, Scottsdale, AZ (US); Robert J. Dempsey, Middleton, MA (US)

(73) Assignee: Inspire Pharmaceuticals, Inc., Whitehouse Station, NJ (US)

( * ) Notice: Subject to any disclaimer, the term of this patent is extended or adjusted under 35 U.S.C. 154(b) by 428 days.

(21) Appl. No.: 12/501,316

(22) Filed: Jul. 10, 2009

(65) Prior Publication Data

US 2010/0022465 A1    Jan. 28, 2010

Related U.S. Application Data

(60) Provisional application No. 61/079,772, filed on Jul. 10, 2008.

(51) Int. Cl.
    *A61K 31/7052*   (2006.01)
(52) U.S. Cl. .......................................... 514/29; 536/7.4
(58) Field of Classification Search .................... 514/29; 536/7.4
    See application file for complete search history.

(56) References Cited

U.S. PATENT DOCUMENTS

| | | | |
|---|---|---|---|
| 6,239,113 | B1 | 5/2001 | Dawson et al. |
| 6,277,829 | B1 | 8/2001 | Asero et al. |
| 6,455,583 | B1 | 9/2002 | Pflugfelder et al. |
| 6,551,584 | B2 | 4/2003 | Bandyopadhyay et al. |
| 6,569,443 | B1 | 5/2003 | Dawson et al. |
| 7,056,893 | B2 | 6/2006 | Roy et al. |
| 7,063,857 | B1 | 6/2006 | Ueno |
| 7,247,623 | B2 | 7/2007 | Yerxa et al. |
| 7,332,470 | B2 | 2/2008 | Fleiszig et al. |
| 2002/0107238 | A1 | 8/2002 | Bandyopadhyay et al. |
| 2003/0206956 | A1 | 11/2003 | Dawson et al. |
| 2004/0266702 | A1 | 12/2004 | Dawson et al. |
| 2005/0054587 | A1 | 3/2005 | Culic et al. |
| 2005/0137205 | A1 | 6/2005 | Van Breen |
| 2005/0164959 | A1 | 7/2005 | Ahmed |
| 2005/0281861 | A1 | 12/2005 | Hughes et al. |
| 2006/0183698 | A1 | 8/2006 | Abelson |
| 2006/0228394 | A1 | 10/2006 | Peyman |
| 2007/0105761 | A1 | 5/2007 | Chappell et al. |
| 2007/0105788 | A1 | 5/2007 | Mrza-Gernhard et al. |
| 2007/0203173 | A1 | 8/2007 | Mudumba et al. |
| 2008/0033008 | A1 | 2/2008 | Ward et al. |
| 2008/0124378 | A1 | 5/2008 | Byrne et al. |
| 2008/0260832 | A1 | 10/2008 | Burke et al. |
| 2008/0268051 | A1 | 10/2008 | Hughes et al. |
| 2008/0286338 | A1 | 11/2008 | Rosenthal et al. |
| 2009/0074786 | A1 | 3/2009 | Dor et al. |
| 2010/0022465 | A1 | 1/2010 | Brubaker et al. |
| 2010/0190734 | A1 | 7/2010 | Brazzell et al. |

FOREIGN PATENT DOCUMENTS

EP    1075837    2/2001

OTHER PUBLICATIONS

Donnenfeld et al. Continuing Medical Education Supplement to Refractive Eyecare, 12(4), Apr. 2008, p. 1-16.*
Henion, F.S. New Drug Bulletin: Azithromycin 1% Ophthalmic Solution, Aug. 17, 2007, Department of Pharmacy Services, University of Utah Hospital.*
Friedlaender et al. Clinical Ophthalmology, 2007, 1(1), p. 3-10.*
BenEzra, D. ed. Blepharitis and Conjunctivitis: Guideline for Diagnosis and Treatment, 2006, Editorial Glosa, p. 57 and p. 209-212.*
Foulks, GN. Eye & Contact Lens, 2003, 29(1S), p. S96-S100.*
American Academy of Ophthalmology, Corneal External Disease Panel (A. Matoba, Chair), *Blepharitis*, 2003.
Azasite® Prescribing Information, form AZA-0289, Rev. Nov. 2008.
Bron et al., "The Contribution of Meibomian Disease to Dry Eye" *The Ocular Surface*, 2:149-164, date: 2004.
Dana et al., "Anti-Inflammatory Activity of Topical Azithromycin on Corneal Innate Immune Responses," ASCRS 10 abstract, Apr. 2010.
Dougherty & McCulley, "Comparative bacteriology of chronic blepharitis," *Br J Ophthal*, 68: 524-8 (1984).
Foulks et al., "Modification of Meibomian Gland Lipids by Topical Azithromycin," abstract and poster ARVO 2009 meeting May 3-7, 2009.
Foulks and Bron, "Meibomian Gland Dysfunction: A Clinical Scheme for Description, Diagnosis, Classification, and Grading," *The Ocular Surf.*, Jul. 2003; 1(3):107-126. Guttman, C., "Favorable profile makes azithromycin a rationale choice for anterior and posterior blepharitis", *Ophthalmology Times*, Mar. 15, 2008, 38-42.
Jacot et al., "Azithromycin Alters ProMMP-2 and TIMP-1 Following Corneal Wounding in an Experimental Animal Model of Diabetic Ocular Complications", ARVO 2009 abstract.
John et al., "Use of Azithromyin Ophthalmic Solution in the Treatment of Chronic Mixed Anterior Blepharitis," *Ann. Ophthalmol.*, 2008, 40(2):68-74.
Luchs, "Efficacy of Topical Azithromycin Ophthalmic Solution 1% in the Treatment of Posterior Blepharitis", *Adv. Ther.*, 2008, 25(9):857-870.
Mah F. et al., "Ocular Antibiotics: MICs and Clinical Efficacy," R. Lindstrom, Editor, *Ocular Surgery News*, Mar. 25, 2008.

(Continued)

*Primary Examiner* — Layla Bland
*Assistant Examiner* — Jonathan S Lau
(74) *Attorney, Agent, or Firm* — Perkins Coie LLP; Viola T. Kung (57) ABSTRACT

The present invention relates to a method for treating non-infectious, inflammatory chronic posterior blepharitis in a subject. The present invention also relates to a method for treating chronic posterior blepharitis in a subject for over two weeks. The method comprises identifying a subject in need thereof, and topically administering to the eye of the subject a pharmaceutical formulation consisting essentially of an effective amount azithromycin. The present invention further relates to a method for treating dry eye secondary to blepharitis in a subject. The method comprises the steps of: identifying a subject suffering from dry eye secondary to posterior blepharitis, and topically administering to the eye of the subject a pharmaceutical formulation comprising an effective amount of azithromycin. The present invention further relates to method for reducing contact lens intolerance of a subject due to blepharitis or dry eye secondary to blepharitis.

21 Claims, 4 Drawing Sheets

OTHER PUBLICATIONS

O'Brien et al., "Newer Horizons in Ocular Anti-Infective Therapy: Progress in the Management of External and Ocular Surface Infections," R. Lindstrom, Editor, Ocular Surgery News, Jun. 10, 2008.

Solomon, K., "Advanced Treatment of Blepharitis and Expert Panel Recommendations," Novel Therapeutic Regimens in Treating Ocular Surface Disease and Blepharits: Supplement to EyeWorld, Sep. 2008, pp. 10-11.

Tabbara et al., "Effects of dehydration on corneal tissue absorption of topical azithromycin in rabbits" Curr Eye Res., Oct. 2005, 30(10): 915-8.

Touhey et al., "Efficacy of Topical Azithromycin Ophthalmic Solution 1.0% in the Treatment of Chronic Blepharitis Patients", ARVO 2009 poster/abstract.

Zhou et al., "Azithromycin suppresses pro-inflammatory mediators stimulated by a TLR2 ligand zymosan in human corneal epithelial cells", ARVO 2009 abstract.

International Search Report for PCT/US09/50311, mailed Sep. 15, 2009.

Extended European Search Report dated Jul. 10, 2012 for Application No. EP 09795262.

Solomon, Kelly D: "New Drop Aimed at Lid Margin Disease", Apr. 1, 2008.

John, Thomas et al.: "Use of Azithromycin Ophthalmic Solution in the Treatment of Chronic Mixed Anterior Blepharitis." Annals of Ophthalmology, vol. 40, No. 2, Jul. 1, 2008.

\* cited by examiner

METHOD OF TREATING BLEPHARITIS

This application claims the benefit of U.S. Provisional Application 61/079,772, filed Jul. 10, 2008; which is incorporated herein by reference in its entirety.

TECHNICAL FIELD

This invention relates to a method of reducing clinical signs and symptoms of chronic posterior blepharitis, preferably inflammatory and not associated with infection, in a subject. The method involves administering to the subject in need thereof an ophthalmic formulation consisting essentially of azithromycin.

BACKGROUND OF THE INVENTION

Blepharitis is a chronic disorder producing inflammation of the anterior and posterior lid margin, with involvement of skin and its related structures (hairs and sebaceous glands), the mucocutaneous junction, and the meibomian glands. It can also affect the conjunctiva, tear film, and the corneal surface in advanced stages and may be associated with dry eye. Blepharitis is commonly classified into anterior or posterior blepharitis, with anterior affecting the lash bearing region of the lids, and posterior primarily affecting the meibomian gland orifices (American American Academy of Opthalmology, *Blepharitis*. 2003; Thygeson, *Arch Opthalmol.*, 1946, 36:938-942; Foulks, *Ocul Surf* 2003; 1(3):107-120). Blepharitis is one of the most common ocular disorders seen by ophthalmologists and has no cure to date or FDA-approved treatments for this condition.

Blepharitis in its mild form is usually undiagnosed and rarely managed. In one study, the prevalence of blepharitis was estimated at 10% in the general population (Claoue, *Eye*, 1997, 11(6):865-868) but is probably higher in the elderly. Between 30% and 50% of patients with blepharitis also have keratoconjunctivitis sicca (Wu, In: Lee D A, Higginbotham E J, eds. *Clinical Guide to Comprehensive Opthalmology*, 1st ed. Thieme Medical Pub, 1999:189). Blepharitis, with or without a dry eye component, is associated with a broad spectrum of ocular symptoms ranging from mild transient irritation to persistent irritation, burning, itching, redness, pain, ocular fatigue and vision disturbances.

Blepharitic changes limited primarily to the posterior lid margin arise predominantly from pathological processes centered around the meibomian glands. The meibomian glands are holocrine glands that supply the lipids, which form the external oily layer of the precorneal tear film. It is the alteration in this excretory process and the composition of tear film lipids that cause the clinical manifestations seen with this disease.

Clinical and laboratory investigations in recent years have identified several forms of meibomian gland disease/dysfunction (MGD). McCulley et al. (*Opthalmology*, 1982, 89: 1173-1180) have described three forms of meibomitis characterized by biomicroscopic changes in the meibomian glands and ducts. "Secondary meibomitis" represents a localized inflammatory response in which the meibomian glands are secondarily inflamed in a spotty fashion from an anterior lid margin blepharitis. Both "meibomian seborrhea" and "primary meibomitis" produce generalized gland dysfunction, but differ with regard to the underlying glandular abnormality. Meibomian seborrhea is characterized by excessive meibomian secretion in the absence of inflammation (hypersecretory form). Primary meibomitis, by contrast, is distinguished by stagnant and inspissated meibomian secretions (obstructive form).

Acne rosacea, seborrheic dermatitis, psoriasis, atopy and hypersensitivity to bacterial products may all contribute to the etiology of blepharitis (Cher, *Mod Med Austr.*, 1997, 52-62). It is generally assumed that infection plays a role in anterior blepharitis (Thygeson, 1946; Dougherty, 1984; Smith, *CLAO J.*, 1995, 21(3):200-207), and cell-mediated immune responses to staphylococcal antigens has been emphasized (Ficker, *Am J Opthalmol.*, 1991, 15; 111(4):473-479).

Dry eye disease is a disorder due to an insufficient quantity of tears. The signs and symptoms of dry eye disease include ocular surface staining, eyelid swelling and redness, ocular irritation and foreign body sensation (gritty or sandy eyes). The quantity of tears can be reduced by either a failure to produce a sufficient amount of tears or by rapid evaporation of the tear film. Bron et al. (The Ocular Surface, 2: 149-164) disclose that the tear film lipid layer is the major barrier to evaporation from the ocular surface. A decrease in the thickness or functional integrity of the tear film may cause evaporative dry eye. Obstructive meibomian gland dysfunction is the most common cause of evaporative dry eye.

It has been suggested that chronic blepharitis can have an inflammatory etiology that is not associated with infection (Seal, *Br J. Opthalmol.*, 1985, 69(8):604-611). Some studies have demonstrated that only a small proportion of patients with meibomian gland dysfunction (Mathers, *Cornea.*, 1996, 15(2): 110-119) and blepharitis have evidence of an active infection or show the production of staphylococcal toxins (Seal, *Opthalmology.*, 1990, 97(12): 1684-1688). Histological studies have detected inflammatory cell infiltrates containing neutrophils and lymphocytes in the corium and epidermis of blepharitis patients. A chronic nongranulomatous inflammatory reaction is observed in most cases of chronic blepharitis and blepharoconjunctivitis (Yanoff, Ocular pathology. 3rd ed. Lippincott Williams & Wilkins Publishers, 1989; 171-172). The pathophysiology of blepharitis is not well understood, but current consensus is that bacteria, altered meibum lipid composition and inflammation are the major contributors to the process.

The inflammatory aspects of blepharitis have been treated with topical steroids as well as systemic tetracycline for three months or longer. However, the well known side effects of steroid use and long term systemic antibiotic use make these treatment regimes less than optimal. Further, antibiotic ointments have been used to treat the overgrowth of normal bacterial flora in this disease. However, topical antibiotic treatment has not been used to address the inflammatory aspects of blepharitis.

Azithromycin is a macrolide antibiotic. AZASITE® (azithromycin ophthalmic solution) is a 1% sterile aqueous topical ophthalmic solution of azithromycin formulated in DURASITE® (polycarbophil, edetate disodium, sodium chloride). AZASITE® is approved by the U.S. Food and Drug Administration (FDA) for treatment of bacterial conjunctivitis, caused by susceptible isolates of CDC coryneform group G, *Haemophilus influenzae, Staphylococcus aureus, Streptococcus mitis* group, and *Streptococcus pneumoniae* (AZASITE® Package Insert, 2007). The recommended dosage regimen for the treatment of bacterial conjunctivitis is as follows: instill 1 drop in the affected eye(s) twice daily, 8 to 12 hours apart for the first 2 days and then instill 1 drop in the affected eye(s) once daily for the next 5 days (AZASITE® Package Insert, 2007).

Despite the high prevalence of the disease, blepharitis is a poorly understood clinical entity. The present therapies such as warm compresses, lid cleansing, oral nutritional supplements, and oral tetracycline antibiotics present compliance difficulties and disappointing results. Therefore, there is a need for an effective and safe method to treat the inflammatory aspects of blepharitis.

SUMMARY OF THE INVENTION

The present invention is directed to a method for treating inflammatory chronic posterior blepharitis, preferably non-infectious, inflammatory chronic posterior blepharitis in a subject. The method comprises identifying a subject suffering from non-infectious, inflammatory chronic posterior blepharitis, and topically administering a pharmaceutical formulation consisting essentially of an effective amount of azithromycin to the eye of the subject.

The present invention is also directed to a method for treating chronic posterior blepharitis in a subject. The method comprises identifying a subject suffering from chronic posterior blepharitis, and topically administering a pharmaceutical formulation consisting essentially of an effective amount azithromycin to the eye of the subject for a period of more than two weeks.

The present methods are effective in reducing the symptoms and/or clinical signs of blepharitis in a subject such as lid debris, redness of eyelid margin, eyelid swelling, plugging of the meibomian gland, and obstructed meibomian gland secretion.

The present invention is further directed to a method for treating dry eye secondary to blepharitis in a subject. The method comprises the steps of: identifying a subject suffering from dry eye secondary to blepharitis, and topically administering to the eye of the subject a pharmaceutical formulation comprising an effective amount of azithromycin.

The present invention is further directed to a method for reducing contact lens intolerance of a subject due to blepharitis or dry eye secondary to blepharitis. The method comprises: identifying a subject suffering from contact lens intolerance due to blepharitis or dry eye secondary to blepharitis, and topically administering to the eye of the subject a pharmaceutical formulation comprising an effective amount of azithromycin.

DETAILED DESCRIPTION OF THE INVENTION

Bacterial infection and inflammation are the two major contributors to the pathophysiology of blepharitis. Prior to the invention disclosed herein, it was not known that topical antibiotics would be effective in treating the non-bacterial-induced chronic inflammatory aspects of blepharitis. As disclosed herein, the inventors have shown that topical azithromycin is surprisingly effective in treating these chronic inflammatory aspects of blepharitis.

The inventors have discovered that topical use of azithromycin in the eyes has strong anti-inflammatory properties, and azithromycin alone (without additional anti-inflammatory agents such as corticosteroids or anti-allergic agents) is effective as a medicament for topically treating a subject suffering from chronic posterior blepharitis, preferably inflammatory posterior blepharitis that is not associated with bacteria infection. The inventors have discovered that treatment with topical azithromycin ophthalmic solution produces high and sustained azithromycin concentrations in various ocular tissues particularly in the eyelids, and thus is effective in treating chronic posterior blepharitis or chronic meibomian gland disease.

The present invention is directed to a method for treating inflammatory chronic posterior blepharitis in a subject. The present invention is preferably directed to a method for treating non-infectious, inflammatory chronic posterior blepharitis in a subject. The method comprises identifying a subject suffering from inflammatory chronic posterior blepharitis, or non-infectious, inflammatory chronic posterior blepharitis, and topically administering to the eye of the subject a pharmaceutical formulation consisting essentially of an effective amount of azithromycin.

"Non-infectious" blepharitis, as used herein, refers to blepharitis patient that is not suffering from a current infection by an active pathogenic bacterial species or by overgrowth of normal bacterial flora. Identifying a non-infectious patient can include means that are well known in the art and can include, but are not limited to: taking a bacterial culture of a patient to assess that the bacterial load is below pathogenic levels for the various species present, or identifying a patient that has gone through a round of antibiotics.

Blepharitis is associated with a broad spectrum of ocular symptoms ranging from mild transient irritation to persistent irritation, burning, itching, redness, pain, ocular fatigue and vision disturbances. Typical clinical signs of blepharitis include lid debris, redness of eyelid margin, eyelid swelling, plugging of the meibomian gland, and obstructed meibomian gland secretion. Redness of eyelid margin, which is a typical sign of acute inflammation, is improved by the present method.

An "effective amount" of azithromycin topically administered to the ocular surface of a subject is an amount effective to reduce the clinical signs and/or symptoms of a disease.

"Chronic" as used herein, refers to a subject having posterior blepharitis or meibomian gland disease for over 4 weeks.

The present invention provides a rapid and effective method to treat inflammatory and non-infectious chronic posterior blepharitis, without the use of a topical steroid. After one to 2 weeks of topical treatment with azithromycin, patients demonstrate reduced lid margin erythema and improvement in the appearance of the meibomian orifices and/or meibomian gland secretions. The rapid and significant improvement is due to the anti-inflammatory activity of azithromycin independent of its antimicrobial effects. The efficacy is also due to the sustained high concentrations of azithromycin in cornea, conjunctive, and lid, after topical administration on the ocular surface, and the high affinity of azithromycin for the tissue. The present invention is more effective than the anti-inflammatory treatment using a tetracycline drug such as oral doxycycline, which takes 6 weeks or longer, often 3 months or longer to produce clinical improvements (Aronowicz, et al., *J. Opthalmol,* 2006, 90:856-860)

The present invention is also directed to a method for treating chronic posterior blepharitis in a subject by treating the subject daily for over two weeks. The method comprises identifying a subject suffering from chronic posterior blepharitis, and topically administering to the eye of the subject a pharmaceutical formulation consisting essentially of an effective amount of azithromycin daily for more than two weeks, at least three weeks, or at least four weeks. In Warnings and Precautions of the product insert of AZASITE® (azithromycin ophthalmic solution, 1%), it warns against the prolonged use of azithromycin ophthalmic solution because it may result in overgrowth of non-susceptible organisms, including fungi. The benefit of prolonged (over two weeks) treatment with a topical azithromycin formulation is unexpected because an acute bacteria infection is typically resolved by azithromycin treatment in one week, and susceptible bacteria would have been eliminated after 7 or 10 days of treatment. However, the inventors have discovered that the effective treatment period of chronic blepharitis with a topical ophthalmic azithromycin formulation is over two weeks; this prolonged treatment is also indicative of the non-infective nature of the pathologic process and allows the anti-inflammatory properties of azithromycin to have their maximal effect on the chronic inflammatory component of posterior blepharitis. As patients with chronic, inflammatory blepharitis do not typically have an active bacterial infection, the risks mentioned above regarding overgrowth of non-susceptible organisms or the generation of newly resistant organisms is considered minimal.

In another embodiment of the invention, a patient is treated intermittently with a topical azithromycin formulation for a time period of longer than two weeks. "Intermittently" as used herein, means that a patient is not treated every day. The intermittent dosing can be every other day, every other two days, every other three days, 2-6 days on and 2-6 days off, one week on and one week off, one week on for every month, etc. One preferred intermittent dosing is once a day for one week in each month. The intermittent dosing is effective because topical azithromycin formulation produces high and prolonged azithromycin concentration in various ocular tissues including eyelids; thus allowing dosing to be skipped. The intermittent dosing provides a benefit of using lower total dosage of azithromycin. In one embodiment, a subject is treated intermittently after the initial daily dosing of two weeks or more than two weeks.

The present invention also provides a method for treating dry eye symptoms or signs, secondary to blepharitis, such as anterior blepharitis, posterior blepharitis, inflammatory posterior blepharitis, and non-infectious inflammatory posterior blepharitis. The method comprises the steps of: identifying a subject suffering from dry eye secondary to blepharitis, and topically administering to the eye of the subject a pharmaceutical formulation comprising an effective amount of azithromycin. The inventors have discovered that by treating inflammation of the ocular surface with a topical application of azithromycin to the eye, the meibomian glands, which are primarily responsible for the production of the lipid layers of the tear film, improve their function and produce a better quality of tear film, thus the dry eye symptoms or signs are reduced. Symptoms of dry eye disease that can be treated by the present method include foreign body sensation (sandiness or grittiness), ocular dryness and ocular burning or pain. Tear-film break-up time (TBUT) is improved after the treatment, indicating a more stable tear film. In one embodiment, a subject is administered with the pharmaceutical formulation daily for at least two weeks, more than two weeks, at least three weeks, or at least four weeks. In another embodiment, a subject is administered with the pharmaceutical formulation intermittently for at least two weeks, more than two weeks, at least three weeks, or at least four weeks. In yet another embodiment, a subject is administered with the pharmaceutical formulation intermittently after the initial daily dosing of at least two weeks.

The present invention is also directed to a method for reducing contact lens intolerance of a subject due to blepharitis or dry eye secondary to blepharitis. In one embodiment, the subject suffers posterior blepharitis or dry eye secondary to posterior blepharitis. In another embodiment, the subject suffers inflammatory posterior blepharitis or dry eye secondary to inflammatory posterior blepharitis. The method comprises the steps of: identifying a subject suffering from contact lens intolerance due to blepharitis or dry eye secondary to blepharitis, and topically administering to the eye of the subject a pharmaceutical formulation comprising an effective amount of azithromycin. In one embodiment, a subject is administered with the pharmaceutical formulation daily for at least two weeks, more than two weeks, at least three weeks, or at least four weeks. In another embodiment, a subject is administered with the pharmaceutical formulation intermittently for at least two weeks, more than two weeks, at least three weeks, or at least four weeks. In yet another embodiment, a subject is administered with the pharmaceutical formulation intermittently after the initial daily dosing of at least two weeks.

Contact lens intolerance limits the time that a subject is able to comfortably wear contact lenses. The method of the present invention increases comfortable contact lens wearing time per day in a subject, increases the total contact lens wearing time per day in a subject, or makes wearing contact lens more comfortable to the user. The improvement in contact lens intolerance can be evaluated by: comfortable contact lens wearing time, total contact lens wearing time, ocular itch, overall eye comfort, and/or frequency of rewetting drop use. The magnitude of the increase of comfortable contact lens use described in this invention depends of the severity of the contact lens intolerance. For example, the present invention enables a subject with a mild contact lens intolerance to comfortably wear contact lenses for an additional 3 to 6 hours, thus allowing the subject to achieve an optimal wearing time of approximately 14 hours per day. The present invention also benefits a subject with a severe contact lens intolerance. In general, the present method can increase the comfortable contact lens wearing time by at least 2-3 hours per day.

The present invention is concerned primarily with the treatment of human subjects, but can also be employed for the treatment of other mammalian subjects, such as dogs, cats, sheep, horses, pigs, goats, and rabbits.

Azithromycin can be administered to the eyes of a patient by any suitable means, but are preferably administered as a liquid or gel suspension in the form of drops, spray or gel, In one embodiment, azithromycin is in the form of drops, and is dropped onto the ocular surface. In another embodiment, azithromycin is contained within a swab or sponge which can be applied to the ocular surface. In another embodiment, azithromycin is contained within a liquid spray or ointment which can be applied to the ocular surface. In another embodiment, azithromycin is injected directly into the lacrimal tissues or onto the eye surface. In a further embodiment, the azithromycin formulation (e.g., in the form of drops) is first applied on a finger tip or other applicator, then applied or rubbed directly onto the lid margin. Alternatively, azithromycin can be applied to the eye via liposomes. Further, azithromycin can be infused into the tear film via a pump-catheter system. Another embodiment of the present invention involves azithromycin contained within a continuous or selective-release device, for example, membranes such as, but not limited to, those employed in the OCUSERT™ System (polymeric ocular inserts for the administration of drugs, Alza Corp., Palo Alto, Calif.). As an additional embodiment, azithromycin can be contained within, carried by, or attached to contact lenses or other compatible controlled release materials, which are placed on the eye.

The concentration of azithromycin included in the topical solution is an amount sufficient to reduce the signs and/or symptoms of blepharitis or dry eye. The azithromycin concentration is preferably in the range of about 0.01-5%, preferably 0.1% to 2%, more preferably about 0.5 to 1.5%, and most preferably about 1% (w/v). "About" as used herein, refers to ±15% of the recited value.

The invention described herein, is not limited to the free base of azithromycin, but also includes pharmaceutically acceptable salts of azithromycin. Pharmaceutically acceptable salts are salts that retain the desired biological activity of azithromycin and do not impart undesired toxicological effects.

The topical solution containing azithromycin can contain a physiologically compatible vehicle, as those skilled in the ophthalmic art can select using conventional criteria. The ophthalmic vehicles include, but are not limited to, saline solution, water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

The preferred ophthalmic formulations of azithromycin suitable for the present method are those disclosed in U.S. Pat. Nos. 6,239,113, 6,569,443 and 7,056,893; the formulations of which are incorporated herein by reference. For example, the formulation is an aqueous polymeric suspension comprising water, azithromycin, and 0.1 to 10% of a polymeric suspending agent. The polymeric suspending agent comprises a water-swellable water-insoluble crosslinked carboxy-vinyl polymer. For example, the polymeric suspending agent comprises least 90% acrylic acid monomers and 0.1% to 5% crosslinking agent. AZASITE® (azithromycin ophthalmic solution), which is a 1% sterile aqueous topical ophthalmic solution of azithromycin formulated in DURASITE® (polycarbophil, edetate disodium, sodium chloride), is the most preferred ophthalmic formulation. The preferred ophthalmic formulations are able to keep prolonged high azithromycin concentration on the ocular surface, thus facilitating its penetration into the eye tissues.

The formulation optionally includes a preservative, such as benzalkonium chloride and other inactive ingredients such as EDTA. For a short term use of less than two weeks, preferably less than one week, benzalkonium chloride has the benefit of increasing the penetration of azithromycin into eye tissues. However, for chronic (over two weeks) use, preferred formulations are those without any preservatives due to the potential for damage to the corneal epithelium that may result from long term, frequent exposure to preservatives such as benzalkonium chloride. The formulations without preservatives are prepared in a unit dose and stored in a single-use container.

The pH of the formulation is adjusted by adding any physiologically and ophthamologically acceptable pH adjusting acids, bases or buffers to within the range of about 5 to 7.5; preferably 6 to 7. Examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, THAM (trishydroxymethylaminomethane), and the like. Salts and buffers include citrate/dextrose, sodium bicarbonate, ammonium chloride and mixtures of the aforementioned acids and bases.

The osmotic pressure of the aqueous ophthalmic composition is generally from about 200 to about 400 milliosmolar (mOsM), more preferably from 260 to 340 mOsM. The osmotic pressure can be adjusted by using appropriate amounts of physiologically and ophthamologically acceptable ionic or non-ionic agents. Sodium chloride is a preferred ionic agent, and the amount of sodium chloride ranges from about 0.01% to about 1% (w/v), and preferably from about 0.05% to about 0.45% (w/v). Equivalent amounts of one or more salts made up of cations such as potassium, ammonium and the like and anions such as chloride, citrate, ascorbate, borate, phosphate, bicarbonate, sulfate, thiosulfate, bisulfate, sodium bisulfate, ammonium sulfate, and the like can be used in addition to or instead of sodium chloride to achieve osmolality within the above-stated range. Further, non-ionic agents such as mannitol, dextrose, sorbitol, glucose and the like can also be used to adjust the osmolality.

The daily dose to treat chronic blepharitis can be divided among one or several unit dose administrations. The daily dose for azithromycin, for example, can range from one drop (about 50 μl), one to four times a day, depending upon the age and condition of the subject. A preferred regimen for azithromycin is one drop of 1% (w/v) solution, about 1 to 2 times a day. For example, a preferred dosage is one drop in each eye twice a day for two days and then once a day thereafter.

When treating posterior blepharitis, the present method can be combined with mechanical therapy such as warm compress or lid hygiene (lid cleansing).

The invention is illustrated further by the following examples which are not to be construed as limiting the invention in scope or spirit to the specific procedures described in it.

EXAMPLES

Example 1

Effect of Azithromycin on Subjects with Posterior Blepharitis

Objectives

The objective of this study was to compare the efficacy of study drug, AZASITE® (azithromycin ophthalmic solution) 1%, in conjunction with mechanical therapy (warm compress) versus mechanical therapy alone over a two week treatment period on the signs and symptoms of subjects with posterior blepharitis.

Subjects

Subjects were 18 years of age or older, and had a clinical diagnosis of moderate to severe posterior blepharitis. Subjects did not have suspected ocular infection, lid structural abnormalities, or have presence of inflammation and/or active structural change in the iris or anterior chamber. A total of 21 subjects were enrolled in the study.

Methods

This was an open-label study. At Visit 1 (Day 1), all subjects were randomized in 1:1 ratio to receive (a) mechanical therapy alone without study drug (Compress group), or (b) drug in combination with mechanical therapy (Combination group), for 14 days. Study drug was administered as one drop in each eye once daily, except on Day 1 and Day 2 the drug was administered as one drop in each eye twice daily. Study drug was self-administered by the subjects.

All subjects were instructed to properly apply mechanical therapy, which consisted of applying a warm compress to each eye for a five to ten minute time period, twice per day for the duration of the study. With the exception of sponsor-supplied AZASITE® and unpreserved tear substitutes, the subjects were prohibited in using any ocular medication during study participation.

Subjects returned at Visit 2 (Day 14), and were examined and rated for the severity of five signs of blepharitis and questioned regarding their perceived overall efficacy of treatment on the signs and symptoms of blepharitis (global assessment of efficacy).

Scores on the Signs of Blepharitis

Investigators rated the severity of the subjects' blepharitis signs at Visit 1 and 2, according to the following five classifications:

Lid Debris (Collarettes, Clumps/Strands)
- (0) Normal: clear eyelid margin
- (1) Mild: occasional fragment (scurf), 1-5 collarettes
- (2) Moderate: few fragments, 6-20 collarettes
- (3) Severe: many fragments, 21-40 collarettes
- (4) Very severe: clumps/strands, >40 collarettes Redness of the Eyelid Margin
- (0) Normal: no redness.
- (1) Mild: slightly dilated blood vessels; vessels colored pink; present in a segment of the eyelid margin.
- (2) Moderate: more apparent dilation of blood vessels; vessel color more intense, whole margin of the eyelid is involved.
- (3) Severe: increased vascularity of the eyelid margin, numerous and obvious dilated blood vessels, deep red in color, whole margin of the eyelid is involved.
- (4) Very severe: clearly increased vascularity of the eyelid margin, large, numerous dilated blood vessels characterized by deep red color, whole margin of the eyelid is involved, noticeable conjunctival hyperemia.

Swelling
- (0) Normal: no swelling of the eyelid tissue.
- (1) Mild: some swelling of the eyelid margin.
- (2) Moderate: diffuse swelling of the eyelid margin.
- (3) Severe: severe swelling of the eyelid margin with alterations in the eyelid folds.
- (4) Very severe: swelling which clearly reduces interpalpebral aperture.

Plugging of the Meibomian Gland (in the Middle Part of Lower Lid)
- (0) Normal: clear orifices of meibomian glands in the middle part of lower lid
- (1) Mild: less than ⅓ of orifices but at least one contain turbid or oily secretions
- (2) Moderate: between ⅓ and ⅔ of orifices contain turbid or oily secretions
- (3) Severe: more than ⅔ of orifices but not all contain turbid or oily secretions
- (4) Very severe: All orifices plugged with turbid or oily secretions Meibomian Gland Secretion
- (0) Normal: minimal clear secretion
- (1) Mild: cloudy
- (2) Moderate: granular
- (3) Severe: paste
- (4) Obstructed: no expressable secretion Total Clinical Outcome Severity Score is defined as the sum of the above five severity scores as described above.

Results

After 14 days of treatment, the Combination group showed significant improvement compared to the Compress treated group in mean Total Clinical Outcome Severity Score (Table 1), meibomian gland plugging, meibomian gland secretions, and redness of the eyelid margin (Table 2). The Combination group also showed improvement as compared to the Compress treated group in the subject-rated global assessment of the efficacy on the signs and symptoms of blepharitis (Table 3). the combination treatment attenuated eyelid redness, a cardinal sign of acute inflammation.

The results showed that the combination treatment attenuated eyelid redness, an important sign of acute inflammation. These findings suggest that the clinical efficacy of azithromycin in blepharitis is mediated at least in part through the modulation of neutrophil functions and production of inflammatory mediators.

TABLE 1

Effects of topical azithromycin in combination with warm compress (Combination) versus warm compress alone (Compress) on total clinical outcome score in blepharitis patients

| Total Severity Score/Eye | Combination | Compress |
|---|---|---|
| Visit 1 (Baseline) | | |
| Mean ± SD | 11.4 ± 1.33 (18) | 10.8 ± 2.00 (22) |
| Median | 12.0 | 11.0 |
| Minimum, Maximum | 9, 13 | 7, 14 |
| Visit 2 | | |
| Mean ± SD | 3.7 ± 2.14 (18) | 9.3 ± 1.52 (22) |
| Median | 3.0 | 9.0 |
| Minimum, Maximum | 0, 8 | 7, 12 |
| Change from Baseline at Visit 2 | | |
| Mean ± SD | −7.7 ± 1.78 (18) | −1.5 ± 1.26 (22) |
| Median | −8.0 | −1.5 |

TABLE 1-continued

Effects of topical azithromycin in combination with warm compress (Combination) versus warm compress alone (Compress) on total clinical outcome score in blepharitis patients

| Total Severity Score/Eye | Combination | Compress |
|---|---|---|
| Minimum, Maximum | −10, −4 | −4, 0 |
| P | | <0.001 |

The total severity score was the sum total of individual severity scores of all 5 signs for each treatment at each visit as presented in Table 1. Number in the parenthesis indicates the number of eyes evaluated. A negative change from baseline indicates improvement. Mean change from the baseline in the combination group were significantly different (P<0.001, ANCOVA) from that in the compress group.

TABLE 2

Effects of topical azithromycin in combination with warm compress (Combination) versus warm compress alone (Compress) on individual clinical signs in blepharitis patients

| Clinical Sign | Treatment | Severity Score/Eye (Mean ± SD) | | | p |
|---|---|---|---|---|---|
| | | Visit 1 | Visit 2 | Change | |
| Lid Debris | Combination | 1.8 ± 0.65 | 0.7 ± 0.75 | −1.1 ± 0.73 | 0.091 |
| | Compress | 1.7 ± 0.77 | 1.2 ± 0.59 | −0.5 ± 0.67 | |
| Lid Redness | Combination | 3.2 ± 0.65 | 1.1 ± 0.64 | −2.2 ± 0.71 | <0.001 |
| | Compress | 3.0 ± 0.65 | 2.7 ± 0.63 | −0.3 ± 0.48 | |
| Lid Swelling | Combination | 0.9 ± 1.02 | 0.2 ± 0.43 | −0.7 ± 0.69 | 0.926 |
| | Compress | 0.2 ± 0.39 | 0.0 ± 0.0 | −0.2 ± 0.39 | |
| Meibomian Plugging | Combination | 3.0 ± 0.69 | 0.9 ± 0.87 | −2.1 ± 1.00 | <0.001 |
| | Compress | 3.0 ± 0.76 | 2.8 ± 0.73 | −0.2 ± 0.59 | |
| Meibomian Secretion | Combination | 2.5 ± 0.92 | 0.8 ± 0.43 | −1.7 ± 0.57 | <0.001 |
| | Compress | 2.8 ± 0.39 | 2.5 ± 0.51 | −0.3 ± 0.46 | |

A statistically significant improvement from baseline in the following clinical signs was observed for patients in the combination group: extent of lid margin redness (p<0.001), meibomian gland plugging (p<0.001), and quality of meibomian gland secretions (p<0.001). No statistically significant differences were observed in patients treated with hot compress alone.

Four patients (44%) treated with the combination had a complete resolution of meibomian gland plugging in at least one eye vs. 0 patients treated with hot compress alone. Two patients (22%) treated with combination had normalization of meibomian gland secretions vs. 0 patients treated with hot compress alone.

TABLE 3

Global efficacy of topical azithromycin in combination with warm compress (Combination) versus warm compress alone (Compress) in blepharitis patients.

| | Number of Patients (%) | |
|---|---|---|
| Patient Response | Combination | Compress |
| Excellent | 2 (22) | 0 |
| Good | 4 (44) | 2 (18) |
| Fair | 2 (22) | 8 (73) |
| Poor | 1 (11) | 1 (9) |
| Deterioration | 0 | 0 |
| Excellent or Good | 6 (67) | 2 (18) |

Nine patients in the combination group and 11 patients in the compress group rated the overall symptomatic relief they experienced at Visit 2 (at the end of a two-week treatment period). 67% of patients treated with the combination rated excellent or good, whereas only 18% of patients treated with warm compress alone rated excellent or good. It was unexpected to see these dramatic improvements in signs and symptoms of chronic blepharitis patients by the topical application of 1% azithromycin in a short period of two weeks.

Example 2

Effect of Azithromycin on Subjects with Chronic Blepharitis

Objectives

The objective of this study was to compare the safety and efficacy of AZASITE® (azithromycin ophthalmic solution, 1%) in conjunction with mechanical therapy versus mechanical therapy alone without the use of AZASITE® over a 4-week treatment period on signs and symptoms in subjects with chronic blepharitis.

Subjects

Subjects were 18 years of age or older, and had a clinical diagnosis of moderate to severe chronic blepharitis, with a clinical sign severity score of at least 2 (moderate) on either redness or swelling (or both) of the eyelid margin and on either eyelid debris or plugging of the meibomian gland (or both). Subjects also had a symptom severity score of at least 2 (moderate) on their self-reported "most bothersome" symptom at baseline and a score of at least 2 (moderate) on any other symptom. Subjects did not have suspected ocular infection, lid structural abnormalities, or have presence of inflammation and/or active structural change in the iris or anterior chamber. A total of 76 subjects were enrolled in the study.

Methods

This was an open-label study. The study design included 6 clinic visits over 6 weeks. Subject eligibility was established at the screening visit (Visit 1/Day 1). At this visit, eligible subjects were randomized to 1 of 2 therapy arms and initiated either 1) treatment of study drug combined with mechanical therapy or 2) mechanical therapy alone. All randomized subjects underwent mechanical therapy for the entire duration of the trial, beginning at Visit 1 and ending at Visit 6. For purposes of this study, mechanical therapy consisted of applying a warm compress to each eye for a 5- to 10-minute time period twice daily (BID). Upon entering the study, subjects who were assigned to receive study drug self-administered 1 drop of AZASITE® in each eye following mechanical therapy and a subsequent second dose 8-12 hours later. Subjects assigned to the study drug treatment arm continued to administer study drug BID on Day 2 and once daily (QD) for the duration of the study treatment period ending at Visit 5 (approximately 29 days total on study drug treatment).

Subjects returned to the clinic on a weekly basis for Visits 2-5 and attended a follow-up visit, Visit 6, 2 weeks following the end of the treatment period. Efficacy assessments performed at every visit included subject-reported symptom scores and investigator-reported scores on the signs of blepharitis.

With the exception of sponsor-supplied AZASITE® and unpreserved tear substitutes, the subjects were prohibited in using any ocular medication during study participation.

Scores on the Signs of Blepharitis

Investigators rated the severity of the subjects' blepharitis signs at Visit 1 and 2, according to the five classifications as listed in Example 1.

Scores on the Symptoms of Blepharitis

Subjects were asked to rate the following blepharitis symptoms at Visit 1 through 6.

Eyelid Itching

Do your eyelids feel itchy?
- (0) None: My eyelids do not feel itchy.
- (1) Mild: Once in a while, my eyelids feel slightly itchy, but I do not have a desire to rub them.
- (2) Moderate: Occasionally, my eyelids feel itchy, and I need to rub them.
- (3) Severe: It is difficult to relieve the sensation of itchiness even when I rub my eyelids.
- (4) Very severe: I have unbearable eyelid itching with an irresistible urge to rub my eyelids.

Foreign Body Sensation/Sandiness, Grittiness

Do you feel like there's something sandy or gritty in your eye?
- (0) None: My eyes do not feel sandy or gritty.
- (1) Mild: I am aware of the surface of my eyes once in a while.
- (2) Moderate: My eyes feel like there is something small in them occasionally.
- (3) Severe: My eyes feel like there is something large or gritty in them.
- (4) Very severe: I am unable to open my eyes due to feeling of a foreign body in my eyes.

Ocular Dryness

Are your eyes feeling dry?
- (0) None: My eyes do not feel dry.
- (1) Mild: I am aware of dryness and have to blink to feel better.
- (2) Moderate: I am aware of dryness and have to use artificial tears occasionally.
- (3) Severe: I am aware of dryness and have to use artificial tears routinely.
- (4) Very severe: I am aware of dryness, I always have to have artificial tears and I use them more than 6 times a day.

Ocular Burning or Pain

Are your eyes burning or painful?
- (0) None: My eyes do not burn or ache.
- (1) Mild: I am aware of the surface of my eyes; they mildly burn or ache.
- (2) Moderate: I feel my eyes are burning, but still tolerable.
- (3) Severe: My eyes feel throbbing or fiery due to burning/pain.
- (4) Very severe: I am unable to open my eyes due to burning/pain.

Swollen/Heavy Eyelids

Do you feel like your eyelids are heavy or swollen?
- (0) Normal: I don't feel that my eyelids are heavy/swollen.
- (1) Mild: I feel that my eyelids are mildly heavy/swollen.
- (2) Moderate: I feel my eyelids are heavy/swollen, but I can tolerate it.
- (3) Severe: I feel my eyelids are heavy/swollen, I like to close my eyes for a few minutes.
- (4) Very severe: I feel my eyelids are heavy/swollen and haw to make an effort to keep my eyes open.

Total Symptom Score is defined as the sum of the above five symptoms severity scores as described above.

Results

Figure 1:
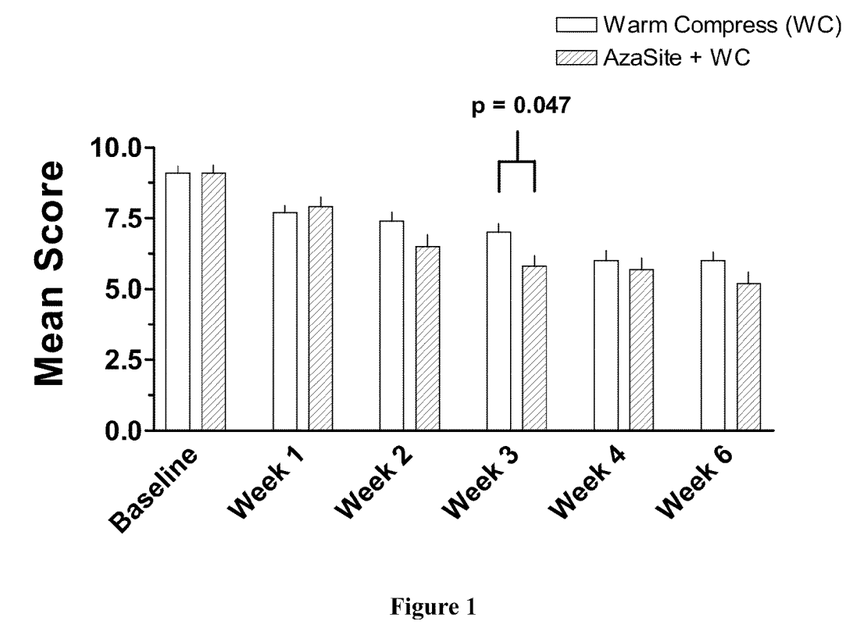
FIG. 1 depicts the mean total sign scores (sum of the five clinical sign severity scores) from subjects treated with topical azithromycin plus warm compresses and subjects treated with warm compresses only (mean±SEM).

Mean decreases from baseline (indicating improvement) in the total clinical sign severity score were observed in both treatment groups at each study visit from Week 1 through Week 6 (FIG. 1). The mean decrease was greater in the AZASITE® plus mechanical therapy group than in the mechanical therapy alone group, at each study visit from Week 2 through Week 6, but the difference was statistically significant only at Week 3 (−3.3 vs. −2.1, p=0.047).

Figure 2:
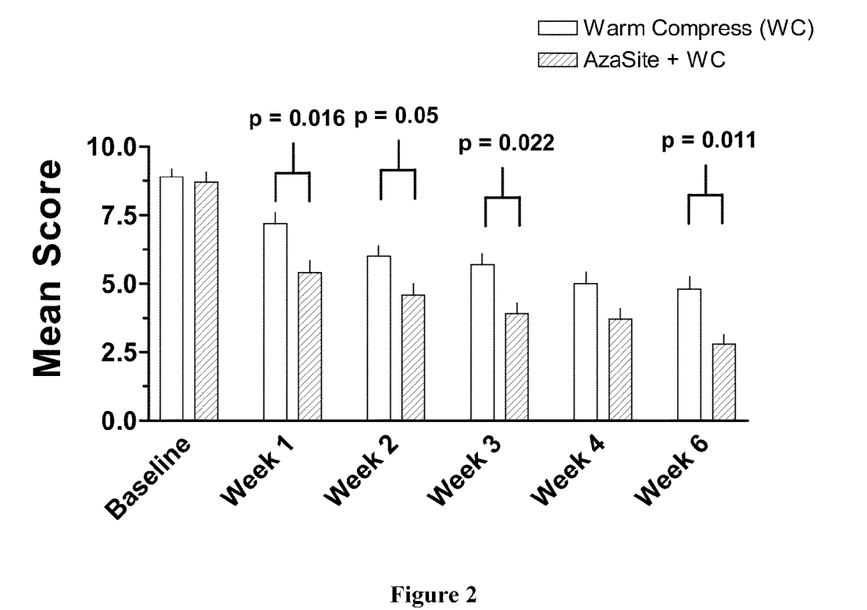
FIG. 2 depicts the mean total symptom scores (sum of the five clinical symptom severity scores) from subjects treated with topical azithromycin plus warm compresses and subjects treated with warm compresses only (mean±SEM).

Improvement in the total symptom severity score was also observed in both treatment groups at each post-baseline visit (FIG. 2). The mean decreases from baseline were statistically significantly (p<0.05) greater in the AZASITE® plus mechanical therapy group versus the mechanical therapy alone group at each study visit from Week 1 (−3.5 vs. −1.8, p=0.016) through Week 6 (−5.9 vs. −4.1, p=0.011), with the exception of a near significant difference at Week 4 (−5.1 vs. −4.0, p=0.090).

Example 3

Modification of Meibomian Gland Lipids by Topical Azithromycin

Objectives

The objective of this study was to assess the effects of AZASITE® (azithromycin ophthalmic solution, 1%) on the physicochemical properties of the meibomian gland secretions in patients with meibomian gland disease (posterior blepharitis).

Subjects

Seventeen adult subjects with symptomatic meibomian gland dysfunction unresponsive to lid massage therapy. A total of 17 subjects were enrolled in the study.

Methods

This was a prospective, open-label, interventional clinical trial using topical azithromycin 1% solution applied once daily for one month of therapy. Clinical examinations were performed at entry, at week 2 and 4 of therapy, and one month following cessation of therapy to evaluate symptoms and signs of MGD. Expression of the meibomian glands was performed at each visit and collected meibum was stored under argon gas in a freezer until spectroscopic analysis. Signs and symptoms were scored on a four point categorical scale.

The collected specimens were analyzed by Fourier Transform Infrared (FTIR), Nuclear Magnetic Resonance (NMR), and Matrix Assisted Laser Desorption Ionization-Time of Flight (MALDI-TOF) spectroscopy.

Clinical data was analyzed as change from baseline by comparison of mean scores using two tailed Student t-test.

Results

Figure 3:
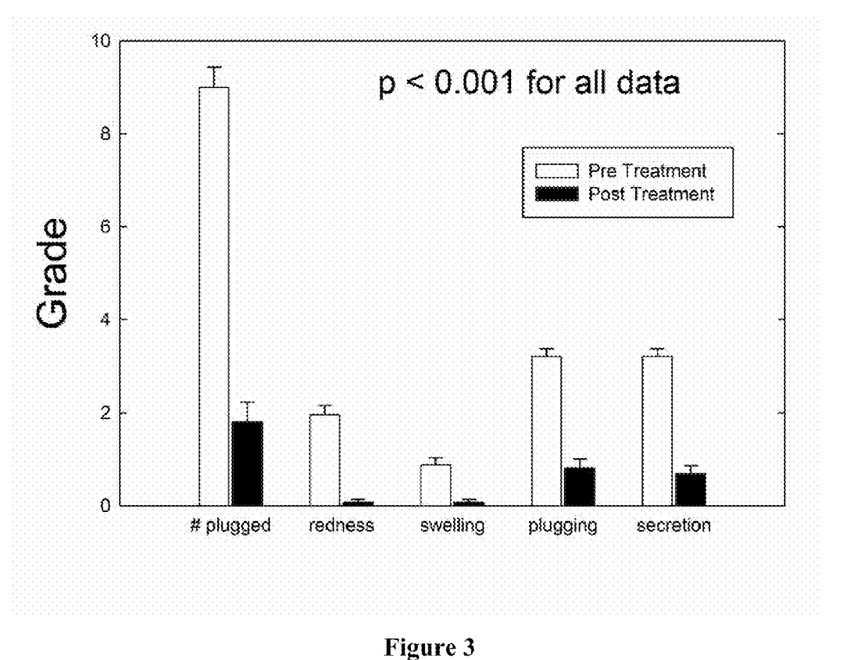
FIG. 3 shows the effect of topical azithromycin treatment on the signs of posterior blepharitis. The mean values for the individual signs are presented as pre and post treatment with once daily dosing of AZASITE® for four weeks (mean±SEM).
Figure 4:
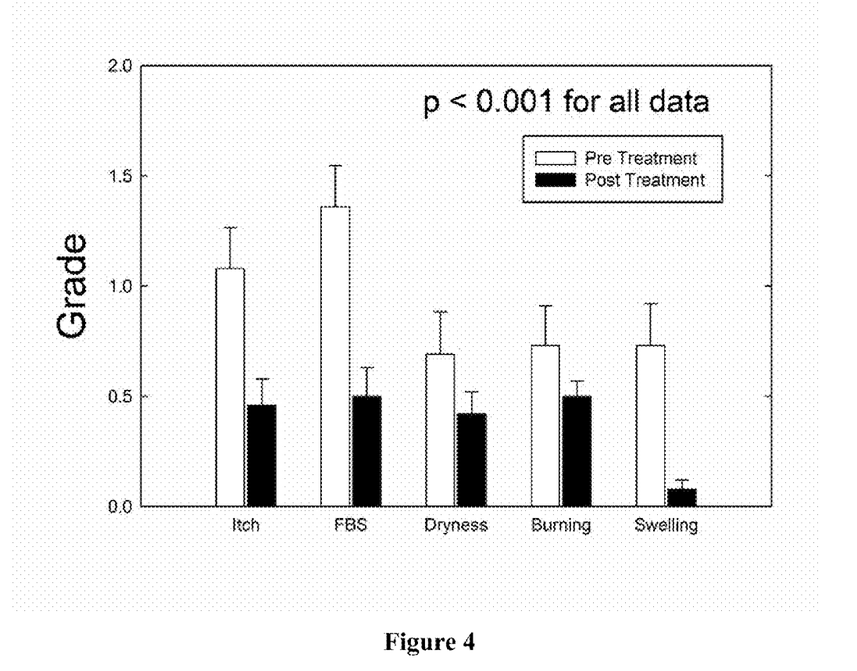
FIG. 4 shows the effect of topical azithromycin treatment on the symptoms of posterior blepharitis. The mean values for the individual symptoms are presented as pre and post treatment with once daily dosing of AZASITE® for four weeks (mean±SEM).

After 4 weeks of AZASITE® treatment, all of the signs (FIG. 3) and symptoms (FIG. 4) of meibomian gland dysfunction tested in this study were significantly improved or resolved. All signs and symptoms were assessed on a 0-4 scale, except the number of glands plugged was evaluated as the number of glands showing plugging from the middle 10 glands in the upper eyelid.

Figure 5:
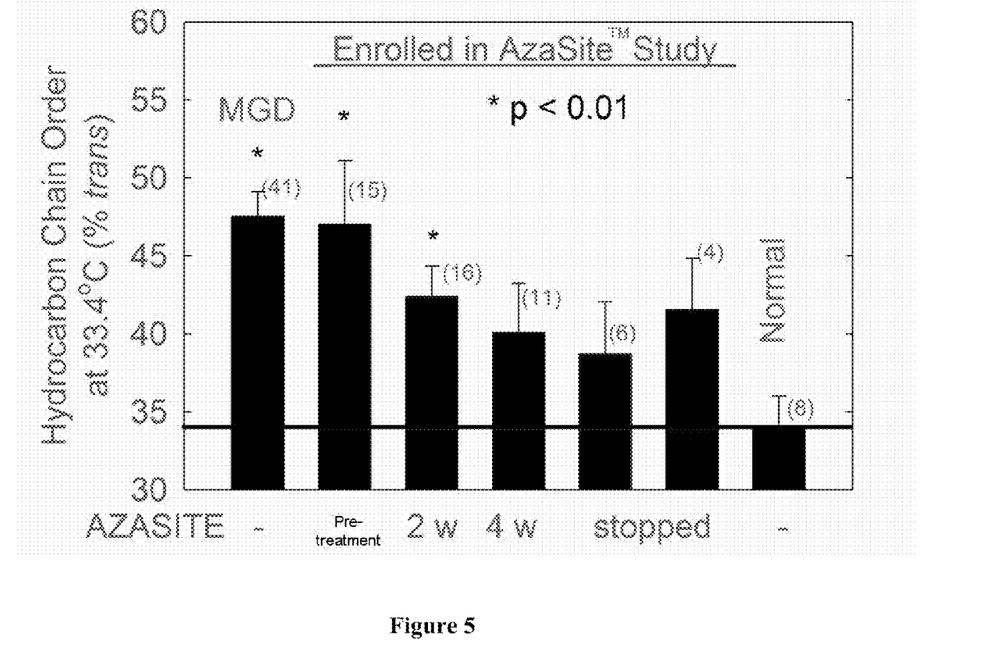
FIG. 5 shows the effect of topical azithromycin treatment for four weeks on the hydrocarbon chain order of meibomian gland lipids. The mean values of the lipid analysis of patients with (i) meibomian gland disease (MGD), (ii) MGD patients treated with topical azithromycin, and (iii) normal subjects (control) are presented (mean±SEM). The numbers in parentheses represent the number of samples analyzed.

MGD subjects were found to have abnormal lipid structure and function prior to therapy with evidence of increased lipid ordering (48% trans rotamers for MGD patients versus 34% for normal patients) (FIG. 5). Treatment with AZASITE® reduced the percentage of trans rotamers in the meibomian gland lipids at two weeks of treatment and continued to improve the lipids towards normal after four weeks of treatment.

Figure 6:
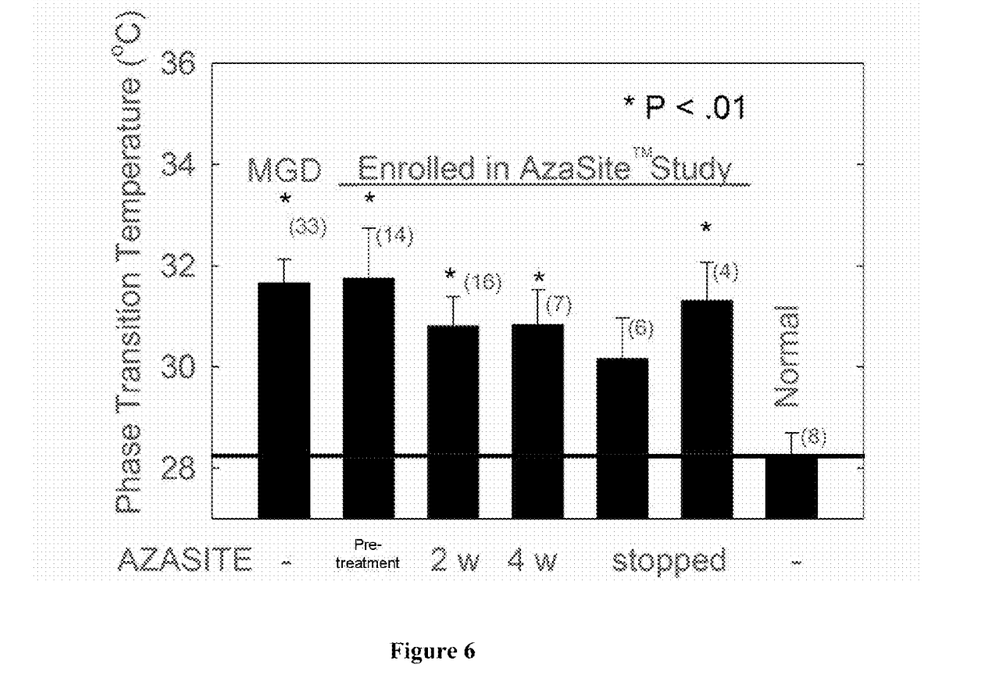
FIG. 6 shows the effect of topical azithromycin treatment for four weeks on the phase transition temperature of meibomian gland lipids. The mean values of the lipid analysis of patients with (i) meibomian gland disease (MGD), (ii) MGD patients treated with topical azithromycin, and (iii) normal subjects (control) are presented (mean±SEM). The numbers in parentheses represent the number of samples analyzed.

MGD subjects were found to have higher phase transition temperature (32° C.) than normals (28° C.). Fourteen subjects were treated a with AZASITE® solution for one month; the subjects showed reduction of the abnormal lipid behavior measured at 2 and 4 weeks of treatment (FIG. 6).

Example 4

Use of Azithromycin for Reducing the Signs and Symptoms of Dry Eye in Patients with Posterior Blepharitis (Meibomian Gland Disease)

Objectives

The objective of this study was to assess the efficacy of study drug, AZASITE® (azithromycin ophthalmic solution, 1%), over a four week treatment period on the signs and symptoms of dry eye disease in subjects with posterior blepharitis.

Subjects

Subjects were 18 years of age or older, and had a clinical diagnosis of moderate to severe posterior blepharitis. A total of 17 subjects were enrolled in the study.

Methods

This was an open-label study. At Visit 1 (Day 1), all subjects were provided AZASITE®. Study drug was administered as one drop in each eye once daily. Study drug was self-administered by the subjects.

Patients were asked to rate their symptoms including: ocular drying, ocular burning/pain, and foreign body sensation at Visit 1 and at Visit 2 (Day 28). Additionally, at each Visit, the investigators assessed the subject's Tear-film Break-Up Time (TBUT).

Scores on the Symptoms of Dry Eye Disease

Patients rated the severity of their dry eye symptoms at Visit 1 and 2 according to the following classifications:

Foreign Body Sensation (FBS)/Sandiness, Grittiness

Do you feel like there's something sandy or gritty in your eye?
 (0) None: My eyes do not feel sandy or gritty.
 (1) Mild: I am aware of the surface of my eyes once in a while.
 (2) Moderate: My eyes feel like there is something small in them occasionally.
 (3) Severe: My eyes feel like there is something large or gritty in them.
 (4) Very severe: I am unable to open my eyes due to feeling of a foreign body in my eyes.

Ocular Dryness

Are your eyes feeling dry?
 (0) None: My eyes do not feel dry.
 (1) Mild: I am aware of dryness and have to blink to feel better.
 (2) Moderate: I am aware of dryness and have to use artificial tears occasionally.
 (3) Severe: I am aware of dryness and have to use artificial tears routinely.
 (4) Very severe: I am aware of dryness, I always have to have artificial tears and I use them more than 6 times a day.

Ocular Burning or Pain

Are your eyes burning or painful?
 (0) None: My eyes do not burn or ache.
 (1) Mild: I am aware of the surface of my eyes; they mildly burn or ache.
 (2) Moderate: I feel my eyes are burning, but still tolerable.
 (3) Severe: My eyes feel throbbing or fiery due to burning/pain.
 (4) Very severe: I am unable to open my eyes due to burning/pain.

Scores on the Signs of Dry Eye Disease

The investigator rated the severity of their dry eye signs at Visit 1 and 2 according to the following classifications:

TBUT

Fluorescein dye was applied to the subject's ocular surface to facilitate the assessment of the subject's TBUT. Via examination with a slit lamp, the subjects were instructed to blink after the administration of the fluorescein and the time until the appearance of the first dry spot was recorded as the TBUT.

Results

Figure 7:
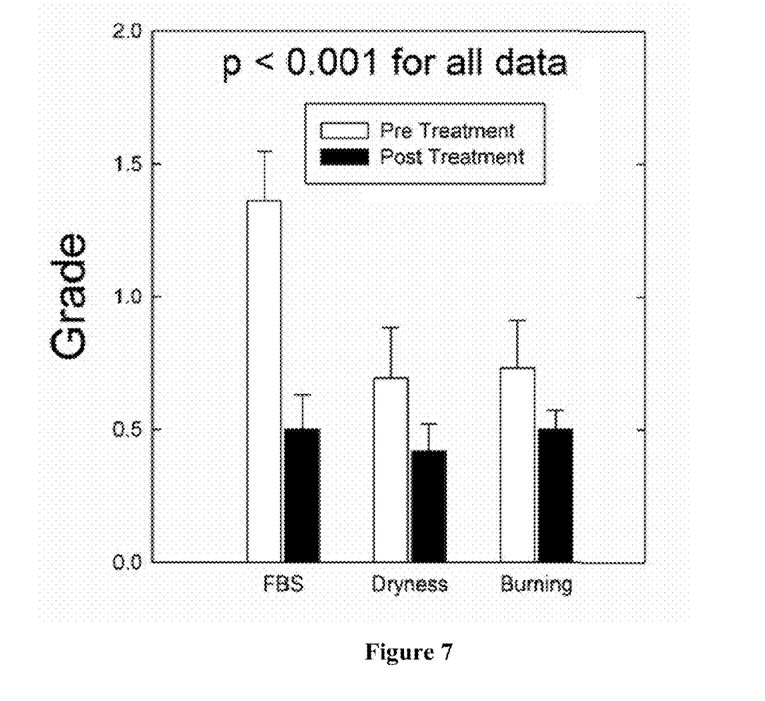
FIG. 7 shows the mean dry eye symptom scores before and after treatment with AZASITE® for 4 weeks (mean±SEM).
Figure 8:
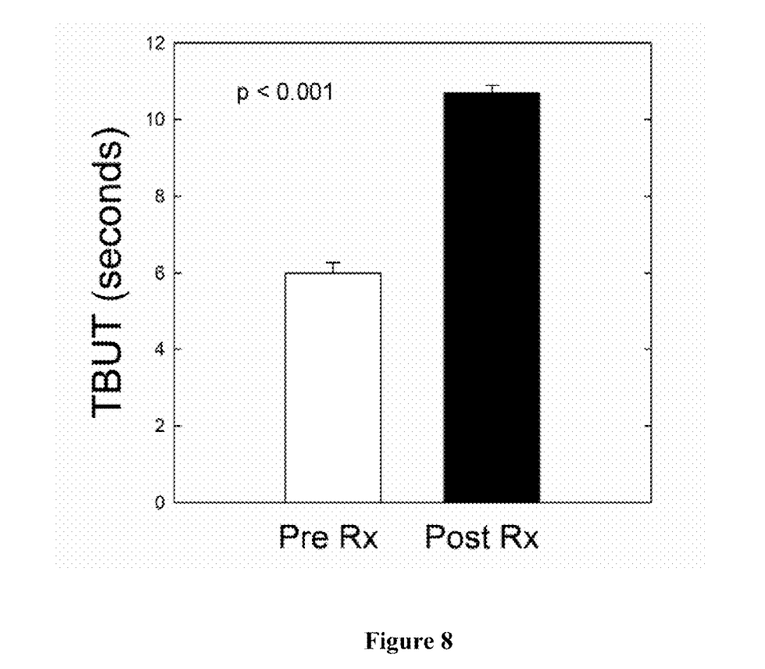
FIG. 8 shows the mean tear break-up time (TBUT) scores before (Pre Rx) and after (Post Rx) treatment with AZASITE® for 4 weeks (mean±SEM).

The mean scores for individual signs and symptoms were compared for Visits 2 (Day 28) to baseline (Visit 1). Significant decreases in the mean scores for the individual dry eye symptoms were observed after treatment with AZASITE® and are presented in FIG. 7 ($p<0.001$; two tailed Student t-test). A significant increase in the TBUT was observed after treatment with AZASITE® and is shown in FIG. 8 ($p<0.001$; two tailed Student t-test).

Conclusions

The above results indicate that treatment with AZASITE® significantly improved the signs and symptoms of dry eye disease in subjects with posterior blepharitis.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:

1. A method for treating non-infectious, inflammatory chronic posterior blepharitis in a subject, comprising:
 identifying a subject suffering from non-infectious, inflammatory chronic posterior blepharitis, and
 topically administering to the eye of the subject a pharmaceutical formulation consisting essentially of an effective amount of azithromycin.

2. The method according to claim 1, wherein said effective amount of azithromycin is about 0.5-1.5% (w/v).

3. The method according to claim 2, wherein said effective amount of azithromycin is about 1% (w/v).

4. The method according to claim 1, wherein said azithromycin is formulated in polycarbophil, edetate disodium, sodium chloride, and water.

5. The method according to claim 1, wherein said subject is administered with the pharmaceutical formulation for at least two weeks.

6. The method according to claim 1, wherein said subject is administered with the pharmaceutical formulation for at least a month.

7. The method according to claim 1, further comprises the step of treating the subject with a mechanical therapy.

8. A method for treating non-infectious, inflammatory chronic posterior blepharitis in a subject, comprising:
   identifying a subject suffering from non-infectious, inflammatory chronic posterior blepharitis, and
   topically administering to the eye of the subject a pharmaceutical formulation consisting essentially of an effective amount of azithromycin for more than two weeks.

9. The method according to claim 8, wherein said effective amount of azithromycin is about 0.5-1.5% (w/v).

10. The method according to claim 9, wherein said effective amount of azithromycin is about 1% (w/v).

11. The method according to claim 8, wherein said azithromycin is formulated in polycarbophil, edetate disodium, sodium chloride, and water.

12. The method according to claim 8, wherein said subject is administered with the pharmaceutical formulation for at least three weeks.

13. The method according to claim 12, wherein said subject is administered with the pharmaceutical formulation for at least four weeks.

14. The method according to claim 8, further comprises the step of treating the subject with a mechanical therapy.

15. A method for treating inflammatory chronic posterior blepharitis in a subject, comprising:
   identifying a subject suffering from non-infectious, inflammatory chronic posterior blepharitis, and
   topically administering to the eye of the subject a pharmaceutical formulation comprising an effective amount of azithromycin intermittently for over two weeks.

16. The method according to claim 15, wherein the pharmaceutical formulation is topically administered intermittently after the initial daily dosing for two weeks.

17. A method for treating dry eye secondary to non-infectious, inflammatory blepharitis in a subject, comprising:
   identifying a subject suffering from dry eye secondary to non-infectious, inflammatory blepharitis, and
   topically administering to the eye of the subject a pharmaceutical formulation comprising an effective amount of azithromycin.

18. The method according to claim 17, wherein said effective amount of azithromycin is about 0.5-1.5% (w/v).

19. The method according to claim 17, wherein said effective amount of azithromycin is about 1% (w/v).

20. The method according to claim 17, wherein said subject is administered with the pharmaceutical formulation daily or intermittently for more than two weeks.

21. A method for reducing contact lens intolerance of a subject due to non-infectious, inflammatory blepharitis or dry eye secondary to non-infectious, inflammatory blepharitis, comprising:
   identifying a subject suffering from contact lens intolerance due to non-infectious, inflammatory blepharitis or dry eye secondary to non-infectious, inflammatory blepharitis, and
   topically administering to the eye of the subject a pharmaceutical formulation comprising an effective amount of azithromycin, whereby the comfortable contact lens wearing time per day in the subject is increased.

* * * * *